(12) United States Patent
Bousvaros et al.

(10) Patent No.: US 10,342,754 B2
(45) Date of Patent: Jul. 9, 2019

(54) SHAVING AID COMPOSITION

(71) Applicant: BIC-VIOLEX SA, Anixi (GR)

(72) Inventors: Gerasimos Bousvaros, Kifissia (GR); Zoi Antoniou, Keratea-attica (GR)

(73) Assignee: BIC-VIOLEX SA, Anixi (GR)

( * ) Notice: Subject to any disclaimer, the term of this patent is extended or adjusted under 35 U.S.C. 154(b) by 0 days.

(21) Appl. No.: 15/560,014

(22) PCT Filed: Apr. 10, 2015

(86) PCT No.: PCT/EP2015/057826
§ 371 (c)(1),
(2) Date: Sep. 20, 2017

(87) PCT Pub. No.: WO2016/162080
PCT Pub. Date: Oct. 13, 2016

(65) Prior Publication Data
US 2018/0064632 A1 Mar. 8, 2018

(51) Int. Cl.
*A61Q 9/02* (2006.01)
*A61K 8/92* (2006.01)
*A61K 8/34* (2006.01)
*A61K 8/81* (2006.01)
*A61K 8/02* (2006.01)
*A61K 8/36* (2006.01)
*A61K 8/46* (2006.01)
*A61K 8/67* (2006.01)
*A61K 8/85* (2006.01)
*B26B 21/44* (2006.01)

(52) U.S. Cl.
CPC .......... *A61K 8/922* (2013.01); *A61K 8/0229* (2013.01); *A61K 8/345* (2013.01); *A61K 8/361* (2013.01); *A61K 8/463* (2013.01); *A61K 8/678* (2013.01); *A61K 8/8111* (2013.01); *A61K 8/8117* (2013.01); *A61K 8/85* (2013.01); *A61Q 9/02* (2013.01); *B26B 21/443* (2013.01); *A61K 2800/28* (2013.01); *A61K 2800/594* (2013.01)

(58) Field of Classification Search
CPC ........................................................ A61Q 9/02
See application file for complete search history.

(56) References Cited

U.S. PATENT DOCUMENTS

| 7,811,553 | B2 | 10/2010 | O'Grady et al. | |
| 2007/0269392 | A1* | 11/2007 | Sunkara | A61K 8/86 424/59 |
| 2012/0216408 | A1* | 8/2012 | Cook | A61K 8/0216 30/41 |

FOREIGN PATENT DOCUMENTS

| EP | 1125697 B1 | 8/2001 |
| WO | 2012051377 A2 | 4/2012 |
| WO | 2014052390 A2 | 4/2014 |

OTHER PUBLICATIONS

International Search Report for PCT/EP2015/057826, dated Oct. 28, 2015.

* cited by examiner

*Primary Examiner* — Micah Paul Young
(74) *Attorney, Agent, or Firm* — Polsinelli PC

(57) ABSTRACT

A shaving aid composition includes a glycol, a humectant, a soap base, a surfactant, about 0.5 to 5% by weight of an emollient, and/or about 0.5 to 4% by weight of a film former; and/or about 0.5 to 4% by weight of a multifunctional polymer. The shaving aid composition is formed into a bar and disposed in front of and at the rear of several blades disposed between a front edge and a rear edge of a cartridge housing of a razor.

19 Claims, 1 Drawing Sheet

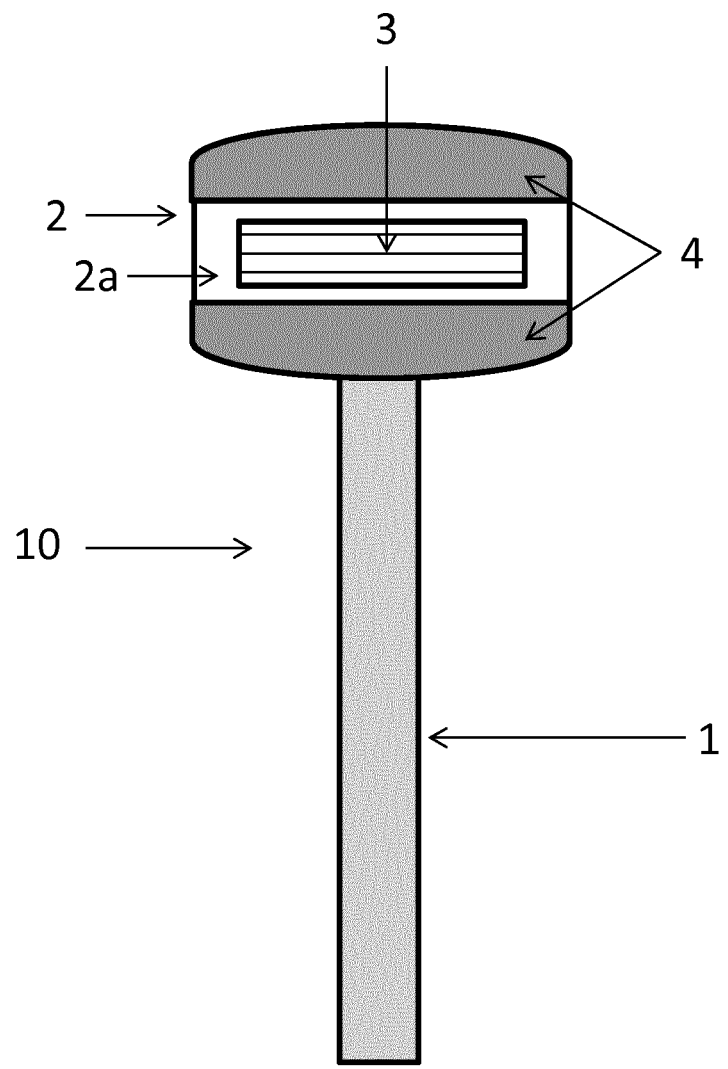

SHAVING AID COMPOSITION

CROSS REFERENCE TO RELATED APPLICATION

This application is a National Stage application of International Application No. PCT/EP2015/057826 filed on Apr. 10, 2015, the entire contents of which is incorporated herein by reference.

BACKGROUND

1. Field

The present disclosure relates to the field of shaving aid compositions. More specifically, the present disclosure relates to a shaving aid composition intended to be attached to a razor head as a shaving bar for an efficient and simplified shave.

2. Description of Related Art

Conventional razors include a lubricating strip having a shaving aid composition. In many instances, the shaving aid composition may not be sufficient to provide a comfortable shave by itself (i.e. without the use of an additional shaving aid).

In addition to conventional razors, other razors are "2 in 1" razors which include "gel bars" to eliminate need for an additional shaving aid, and razors with a skin conditioning solid which lathers while shaving.

Many of the existing razor products include bulky heads or shaving aid formulas which leave an unpleasant sensation such as, for example, "slimy" residuals on the surface of the skin. Also, many of the current shaving aid formulas have a high dissolve rate which limits the number of shaves before reaching its fully designed life of use. On the other hand, there are some current razors with a low dissolve rate which does not provide sufficient aid to the user in order to shave adequately and without additional shaving aids during each shave. Hence, users oftentimes resort to incorporating other functional components in order to achieve a desirably efficient shave.

SUMMARY

Aspects of the disclosure may include a shaving aid composition that may not require the use of an additional shaving aid in order to achieve an efficient shave. The shaving aid composition may include:
  a glycol,
  a humectant,
  a soap base, and
  a surfactant,
  the shaving aid composition may further include:
  about 0.5 to 5% by weight, for example, about 0.5 to 0.8% by weight of an emollient, and/or
  about 0.5 to 4%, for example, 1.5 to 3.5% by weight of a film former; and/or
  about 0.5 to 4% by weight, for example, 2.5 to 3.5% of a multifunctional polymer;
  Unless otherwise specified, all percentages and amounts expressed herein and elsewhere in the specification should be understood to refer to percentages by weight calculated with respect to the total weight of the shaving aid composition.

The shaving aid composition according to aspects of the disclosure may increase shaving quality and performance, by improving glideness, skin smoothness and skin conditioning.

Furthermore, the shave aid composition according to aspects of the disclosure may include a dissolve rate balance that may reduce the slimy residue that may exist in some current products.

BRIEF DESCRIPTION OF THE DRAWINGS

FIG. 1 is a front view of a razor having a razor cartridge including a shaving bar made from the shaving aid composition according to aspects of the disclosure.

DETAILED DESCRIPTION

Aspects of the shaving aid composition may include:
  a glycol,
  a humectant,
  a soap base, and
  a surfactant.

The shaving aid component may also include percentages by weight of an emollient, a film-former, a multifunctional polymer, and other components as detailed herein below.

Glycol

Aspects of the shaving aid composition may also include a glycol which may act as a viscosity adjuster and/or as a solvent and/or as a skin conditioning agent.

According to some aspects, glycol may be selected from the group consisting of propylene glycol, ethylene glycol, diethylene glycol and mixtures thereof.

According to other aspects, the shaving aid composition may include propylene glycol.

According to further aspects, the shaving aid composition may include a glycol in an amount of, for example, 20-35% by weight. According to further aspects, the composition may include, for example, an amount of 24-30% by weight.

Humectant

Aspects of the shaving aid composition may also include a humectant which may impart hydrating properties.

According to some aspects, Humectant(s) may be used in an amount, for example, of about 30-50% by weight. According to other aspects, for example, an amount of 33-38% by weight.

According to aspects of the disclosure, Humectants useful in the shaving aid composition may include polyhydric alcohols selected from the group consisting of glycerin, sorbitol and mixture thereof.

According to some aspects, the shaving aid composition may include a mixture of sorbitol and glycerin.

Humectants may include other components such as Aloe Vera powder, for example, in an amount of 0.001-0.05% by weight and/or shea butter, for example, in an amount of 0.2-1% by weight.

According to some aspects, the shaving aid composition may include, for example, a mixture of 15-25% by weight of sorbitol. According to further aspects, 15-18% by weight of sorbitol and 15-25% by weight of glycerin. According to other aspects, the shaving aid composition may include, for example, 16-20% by weight of glycerin. The high amount of glycerin may provide notable comfort to the skin.

Soap Base

According to some aspects, a variety of solid soap bases may also be employed in the shaving aid composition.

Useful soap bases may include fatty acid ester in C10-C24. According to further aspects, useful soap bases may include, for example, C14-C24 such as sodium and/or potassium cocoate, stearate, palmitate, myristate and mixtures thereof.

According to other aspects, the soap base may be a sodium stearate soap base.

According to aspects, the soap base may be, for example, in an amount of 15-24% by weight, while according to other aspects, in an amount of 18-22% by weight.

Surfactant

According to some aspects, a Surfactant(s) may be included in the shaving aid composition. Surfactant(s) may provide cleansing and emulsifying properties.

Surfactant(s) useful in the is the shaving aid composition may include an anionic surfactant. According to further aspects, the surfactant(s) may include, for example, sodium laureth sulfate. The surfactant used in the shaving aid composition may include, for example, an amount of 6.5-12.5% by weight. According to further aspects, the surfactant(s) may include, for example, an amount of 8-12% by weight.

Emollient

Aspects of the shaving aid composition may include an emollient may bring softness, emolliency and spreadability to the composition. The emollient may be hydrogenated polydecene.

According to some aspects; the emollient may be a hydrogenated polydecene that may be commercially available, such as for example, Dekanex®. The shaving aid composition may include Dekanex®, for example, in an amount of 0.5 to 5% by weight. According to further aspects, the amount of Dekanex® may be, for example, 0.5 to 0.8% by weight. According to other aspects, for example, an amount of 0.7% by weight.

Film Former

Aspects of the shaving aid composition may also include a film former which may improve water resistance and rub resistance.

According to some aspects, the film former may be a mixture including, for example, hydrogenated polycyclopentadiene, polyethylene, copernica cerifera wax and tocopherol.

According to other aspects, the film former may be a mixture including hydrogenated polycyclopentadiene, polyethylene, copernica cerifera wax and tocopherol, that may be commercially available such as, for example, Koboguard HRPC®. The shaving aid composition may include Koboguard HRPC®, for example, in an amount of 0.5 to 4% by weight. According to some aspects, the amount of Koboguard HRPC® may be, for example, 1.5 to 3.5% by weight. According to other aspects, an amount of 2% by weight.

Multifunctional Polymer

Aspects of the shaving aid composition may also include a multifunctional polymer which may improve foam aesthetics and the feeling of skin.

According to some aspects, the multifunctional polymer may be polypropylene terephthalate.

According to other aspects; the multifunctional polymer may be selected from the group consisting of polypropylene terephtalate, that may be commercially available such as, for example, Aristoflex PEA®. The shaving aid composition may include Aristoflex PEA®, for example, in an amount of 0.5 to 4% by weight. According to other aspects, the Aristoflex PEA® may be, for example, an amount of 2.5 to 3.5% by weight. According to further aspects, for example, an amount of 3% by weight.

Other Components

According to some aspects, the shaving aid composition may also include at least one additional component that may be added to impart specific properties such as coloring agent, fragrance, chelating agent, opacifier, antibacterial agent, or exfoliating particles.

The coloring agents used may be in very low range, and may be typically selected from those used in a range from about 0.0001% to about 0.001% by weight.

Fragrance may also be used in very low range. Fragrances selected may be in a range of, for example, no more than 0.5% by weight.

According to aspects where the shaving aid composition may include a chelating agent. The chelating agent included may be in a range of from 0.05% to 0.2% by weight. Different chelating agents, well known in the art in the cosmetic field, may be employed in the shaving aid composition, such as for example, Dissolvine GL47S®.

According to aspects where the shaving aid composition may include an opacifier. The opacifier included may be in a range of from 0.2% to 2% by weight. Different opacifiers, well-known in the art in the cosmetic field, may be employed in the shaving aid composition, such as for example, Opulyn 301®.

According to some aspects, the shaving aid composition may include:
- about 20-35% by weight of a glycol, and according to further aspects, 24-30% by weight of a glycol;
- about 30-50% by weight of a humectant, and according to further aspects, 33-38% by weight of a humectant
- about 15-24% by weight of a soap base, and according to further aspects, 18-22% by weight of a soap base,
- about 6.5-12.5% by weight of a surfactant, and according to further aspects, 8-12% by weight of a surfactant,
- about 0.5-5% by weight of hydrogenated polydecene, and according to further aspects, 0.5-0.8% of hydrogenated polydecene,
- about 0.5-4% by weight of polypropylene terephthalate, and according to further aspects, 2.5-3.5% of polypropylene terephthalate; and
- about 0.5-4% by weight of a mixture comprising hydrogenated polycyclopentadiene, polyethylene, copernica cerifera wax and tocopherol, and according to further aspects, 1.5-3.5% of a mixture comprising hydrogenated polycyclopentadiene, polyethylene, copernica cerifera wax, and tocopherol.

According to other aspects, the shaving aid composition may include:
- about 20-35% by weight of propylene glycol, and according to further aspects, 24-30% by weight of propylene glycol;
- about 15-25% by weight of glycerin, and according to further aspects, 16-20% by weight of glycerin,
- about 15-25% by weight of sorbitol, and according to further aspects, 15-18% by weight of sorbitol,
- about 15-24% by weight of sodium stearate, and according to further aspects, 18-22% by weight of sodium stearate,
- about 6.5-12.5% by weight of sodium laureth sulfate, and according to further aspects, 8-12% by weight of sodium laureth sulfate,
- about 0.5-5% by weight of hydrogenated polydecene, and according to further aspects, 0.5-0.8% of hydrogenated polydecene,
- about 0.5-4% by weight of polypropylene terephthalate, and according to further aspects, 2.5-3.5% of polypropylene terephthalate; and about 0.5-4% by weight of a mixture comprising hydrogenated polycyclopentadiene, polyethylene, copernica cerifera wax and tocopherol, preferably 1.5-3.5% of a mixture comprising hydrogenated polycyclopentadiene, polyethylene, copernica cerifera wax and tocopherol.

The shaving aid composition may be manufactured by the following method including the steps consisting of:
(i) dissolving a film former in a first amount of glycol to form a first mixture;
(ii) preparing a second mixture including a second amount of glycol with a humectant;
(iii) adding the first mixture to the second mixture;
(iv) adding a surfactant;
(v) adding an emollient and a multifunctional polymer to the mixture obtained in step (iv); and
(vi) optionally adding additional components selected from the group consisting of coloring agent, fragrance, chelating agent, opacifier, antibacterial agent and exfoliating particles to the mixture obtained in step (v).

According to further aspects, the method may also include forming a shaving bar from the shaving aid composition using a process that may be well-known by a person skilled in the art, such as for example, by extrusion or by molding.

Another aspect of the disclosure may involve a razor cartridge including:
a housing having a front edge and a rear edge;
one or more shaving blades between the front edge and the rear edge; and
at least one shaving bar disposed in front of the blade(s) and/or at rear of the blade(s), the shaving bar being made of the shaving aid composition as previously defined herein.

According to further aspects, the shaving bar may be disposed in a shaving bar holder.

According to other aspects, the razor cartridge may include two shaving bars, one disposed in front of the blade(s) and another disposed at rear of the blade(s).

According to other aspects, the razor cartridge may include an additional strip, such as for example, a lubricating strip disposed between the blade(s) and the shaving bar.

Another aspect of the disclosure may involve a razor including:
a handle, and
a razor cartridge as previously defined herein.

According to some aspects, as shown in FIG. 1, a razor 10 may include a handle 1 and a razor cartridge 2 having a housing 2a. The housing 2a may include a front edge and a rear edge. Several blades 3 may be disposed between the front edge and the rear edge of the housing 2a. A shaving bar 4 may be disposed in front of the blades 3 and another shaving bar 4 may be disposed at the rear of the blades 3. The shaving bars 4 may be made of the shaving aid composition disclosed herein.

According to further aspects, contact of the shaving bar with water may cause foam to be formed when the shaving bar may be in contact with the skin, thereby providing an efficient and pleasant shaving experience without the need of an additional shaving aid.

According to other aspects, a shaving aid composition including a mixture of about 0.5 to 5% by weight of an emollient, and/or about 0.5 to 4% of a film former; and/or about 0.5 to 4% of a multifunctional polymer may be used for providing softness, emolliency and spreadability.

Example 1

The shaving aid composition of the present disclosure was prepared by a hot mix of the components described in the table below, where Opulyn® 301 includes Styrene/acrylic copolymer, Residual monomers and water.

TABLE 1

| shaving aid composition of example 1 | |
| --- | --- |
| Components | Amount (%) w |
| Propylene glycol | 20%-35% |
| Glycerin | 15%-25% |
| Sodium stearate | 15%-24% |
| Sorbitol | 15%-25% |
| Sodium Polyoxyethylene Laurylether Sulfate | 6.5%-12.5% |
| Hydrogenated Polycyclopentadiene | 1.6 |
| Polyethylene | |
| Copernicia Cerifera (Carnauba) Wax | |
| Tocopherol | |
| hydrogenated polydecene | 0.5 |
| Polypropylene Terephthalate | 2.5 |
| Opulyn 301 ® | 0.2%-2% |
| Shea butter | 0.2%-1% |
| Aloe vera powder | 0.001%-0.05% |
| Perfume | <0.5% |
| Dissolvine GL47S ® | 0.05%-0.2% |
| Color | 0.0001%-0.001% |

The invention claimed is:

1. A shaving aid composition comprising:
a glycol;
a humectant;
a soap base;
a surfactant;
about 0.5% to about 5% by weight of an emollient;
about 0.5% to about 4% by weight of a film former comprising a mixture including at least hydrogenated polycyclopentadiene and copernica cerifera wax; and
about 0.5% to about 4% by weight of a multifunctional polymer;
wherein the percentages by weight are calculated with respect to a total weight of the shaving aid composition.

2. The shaving aid composition according to claim 1, wherein the emollient is hydrogenated polydecene.

3. The shaving aid composition according to claim 1, wherein the film former is a mixture further including polyethylene, and tocopherol.

4. The shaving aid composition according to claim 1, wherein the multifunctional polymer is polypropylene terephthalate.

5. The shaving aid composition according to claim 1, wherein the composition includes an amount of about 20% to about 35% by weight of the glycol.

6. The shaving aid composition according to claim 5, wherein the glycol is propylene glycol.

7. The shaving aid composition according to claim 1, wherein the composition includes an amount of about 30% to about 50% by weight of the humectant.

8. The shaving aid composition according to claim 1, wherein the composition includes an amount of about 15% to about 24% by weight of the soap base.

9. The shaving aid composition according to claim 1, wherein the composition includes an amount of about 6.5% to about 12.5% by weight of the surfactant.

10. The shaving aid composition according to claim 7, wherein the humectant is selected from the group consisting of glycerin, sorbitol and mixtures thereof.

11. The shaving aid composition according to claim 10, wherein the humectant is a mixture of the glycerin and the sorbitol.

12. The shaving aid composition according to claim 8, wherein the soap base is selected from the group consisting of fatty acid ester in C10-C24.

13. The shaving aid composition according to claim 12, wherein the soap base is selected from the group consisting of sodium, potassium cocoate, stearate, palmitate, myristate, and mixtures thereof.

14. The shaving aid composition according to claim 13, wherein the soap base is sodium stearate.

15. The shaving aid composition according to claim 9, wherein the surfactant is sodium laureth sulfate.

16. The shaving aid composition according to claim 1, comprising:
    about 20% to about 35% by weight by weight of the glycol;
    about 30% to about 50% by weight by weight of the humectant;
    about 15% to about 24% by weight by weight of the soap base;
    about 6.5% to about 12.5% by weight by weight of the surfactant;
    about 0.5% to about 5% by weight of a hydrogenated polydecene;
    about 0.5% to about 4% by weight of a polypropylene terephthalate; and
    about 0.5% to about 4% by weight of a mixture comprising hydrogenated polycyclopentadiene, polyethylene, copernica cerifera wax and tocopherol,
    wherein the percentages by weight are calculated with respect to a total weight of the shaving aid composition.

17. The shaving aid composition according to claim 1, comprising:
    about 20% to about 35% by weight by weight of a propylene glycol;
    about 15% to about 25% by weight by weight of a glycerin;
    about 15% to about 25% by weight by weight of a sorbitol;
    about 15% to about 24% by weight of a sodium stearate;
    about 6.5% to about 12.5% by weight of a sodium laureth sulfate;
    about 0.5% to about 5% by weight of a hydrogenated polydecene;
    about 0.5% to about 4% by weight of a polypropylene terephthalate; and
    about 0.5% to about 4% by weight of a mixture comprising hydrogenated polycyclopentadiene, polyethylene, copernica cerifera wax, and tocopherol,
    wherein the percentages by weight are calculated with respect to a total weight of the shaving aid composition.

18. The shaving aid composition according to claim 1, further comprising at least one additional component selected from the group consisting of a coloring agent, fragrance, chelating agent, opacifier, antibacterial agent, or exfoliating particles.

19. A razor cartridge comprising:
    a housing having a front edge and a rear edge;
    one or more shaving blades between the front edge and the rear edge; and
    at least one shaving bar disposed in front of the one or more shaving blades and at least another shaving bar disposed at a rear of the one or more shaving blades, the at least one shaving bar and the at least another shaving bar being made of the shaving aid composition according to claim 1.

* * * * *